US009528876B2

United States Patent
Micheels

(10) Patent No.: US 9,528,876 B2
(45) Date of Patent: Dec. 27, 2016

(54) SOLID STATE BROAD BAND NEAR-INFRARED LIGHT SOURCE

(71) Applicant: Innovative Science Tools, Inc., Concord, MA (US)

(72) Inventor: Ronald H Micheels, Concord, MA (US)

(73) Assignee: Innovative Science Tools, Inc., Concord, MA (US)

( * ) Notice: Subject to any disclaimer, the term of this patent is extended or adjusted under 35 U.S.C. 154(b) by 0 days.

(21) Appl. No.: 14/860,259

(22) Filed: Sep. 21, 2015

(65) Prior Publication Data

US 2016/0091367 A1   Mar. 31, 2016

Related U.S. Application Data

(60) Provisional application No. 62/056,941, filed on Sep. 29, 2014.

(51) Int. Cl.
  *G01J 3/00* (2006.01)
  *G01J 3/10* (2006.01)

(52) U.S. Cl.
  CPC ..................... *G01J 3/108* (2013.01)

(58) Field of Classification Search
  CPC ............ G01J 3/108; F21V 7/22; F21V 7/043; F21V 9/16; F21V 2200/10; F21K 9/56; F21Y 2101/02

(Continued)

(56) References Cited

U.S. PATENT DOCUMENTS 5,218,609 A * 6/1993 Oda ................... H01S 3/115
                                                     372/10
5,966,393 A   10/1999 Hide et al.
(Continued)

FOREIGN PATENT DOCUMENTS

CN    103450894 A    12/2013
WO   2010053341 A1    5/2010

OTHER PUBLICATIONS

Faulkner et al. "Lanthanide Complexes for Luminescence Imaging Applications." Applied Spectroscopy Reviews, vol. 40, 2005, pp. 1-31, online: http://www.bioee.ee.columbia.edu/courses/upload/Bibliography/faulker_appliedspectroscopy_2005.pdf.

(Continued)

*Primary Examiner* — David Porta
*Assistant Examiner* — Gisselle Gutierrez
(74) *Attorney, Agent, or Firm* — Clocktower Law; Eric J. Heels; Michael A. Bartley

(57) ABSTRACT

A light source for near-infrared transmission and reflection spectroscopy can be constructed from a combination of a high power blue or blue-green light emitting diode (LED) and a phosphor element based on an inorganic material. The phosphor element absorbs the LED light and, in response to the LED excitation, emits luminescence that continuously covers the 700-1050 nm range. One possible material that can be used for such a near-infrared emitting phosphor element is a single crystal rod of Ti+3 doped Sapphire. An alternative near-infrared emitting phosphor material is a disk or rectangular shaped composite of $Ti^{+3}$ doped Sapphire powder embedded in a clear optical epoxy or silicone encapsulant. Such a combination of a blue LED for excitation of a phosphor element that emits in a broad wavelength band has been widely used in white LEDs where the emission is in the 400-700 nm range.

12 Claims, 19 Drawing Sheets

(58) Field of Classification Search
USPC .............. 250/339.07, 458.1, 459.1; 364/84
See application file for complete search history.

(56) References Cited

U.S. PATENT DOCUMENTS

| | | | |
|---|---|---|---|
| 6,417,019 | B1 | 7/2002 | Mueller et al. |
| 6,670,748 | B2 | 12/2003 | Ellens et al. |
| 6,850,013 | B1 | 2/2005 | Ashley et al. |
| 7,682,848 | B2 | 3/2010 | Shimizu et al. |
| 7,795,625 | B2 | 9/2010 | Suzuki |
| 7,887,718 | B2 | 2/2011 | Nagatomi et al. |
| 8,471,459 | B2 | 6/2013 | Kato et al. |
| 8,475,682 | B2 | 7/2013 | Nagatomi et al. |
| 8,853,712 | B2 | 10/2014 | Hussell et al. |
| 2002/0167485 | A1* | 11/2002 | Hedrick ............ G02B 27/01 345/156 |
| 2002/0185603 | A1 | 12/2002 | Daly et al. |
| 2005/0161694 | A1 | 7/2005 | Reeh et al. |
| 2010/0102707 | A1 | 4/2010 | Fukuda et al. |
| 2012/0099102 | A1 | 4/2012 | Bello |
| 2012/0300432 | A1 | 11/2012 | Matsubayashi et al. |
| 2013/0050980 | A1 | 2/2013 | Kato et al. |
| 2013/0056775 | A1 | 3/2013 | Kawakami |
| 2013/0127333 | A1 | 5/2013 | Jia et al. |
| 2013/0160855 | A1* | 6/2013 | Gibson ............ H01G 9/2031 136/263 |
| 2013/0314893 | A1* | 11/2013 | Paquette ............ G02F 1/353 362/84 |
| 2013/0326941 | A1 | 12/2013 | Pickett et al. |
| 2014/0084782 | A1 | 3/2014 | Fukuda et al. |
| 2014/0265818 | A1 | 9/2014 | Okada et al. |
| 2016/0027969 | A1* | 1/2016 | Denis ............ H01L 33/0095 257/98 |

OTHER PUBLICATIONS

Punke et al. "High-repetition-rate white-fight pump probe spectroscopy with a tapered fiber." Optics Letters vol. 31, No. 8, Apr. 15, 2006; pp. 1157-1159, online: http://www.dmphotonics.com/Punke_OL_2006.pdf.

* cited by examiner

SOLID STATE BROAD BAND NEAR-INFRARED LIGHT SOURCE

CROSS-REFERENCE TO RELATED APPLICATIONS

This utility patent application claims priority from U.S. provisional patent application Ser. No. 62/056,941, filed Sep. 29, 2014, titled "Solid State Broad Band Near-Infrared Light Source" naming inventor Ronald H. Micheels. The disclosures herein can be used in various applications, including the systems described in U.S. Pat. Pub. No. 2013/0265568, "OPTICAL ANALYZER FOR IDENTIFICATION OF MATERIALS USING TRANSMISSION SPECTROSCOPY", published Oct. 10, 2013, naming inventors Ronald H. Micheels and Don J. Lee, and U.S. Pat. No. 8,859,969, "OPTICAL ANALYZER FOR IDENTIFICATION OF MATERIALS USING REFLECTANCE SPECTROSCOPY", issued Oct. 14, 2014, naming inventors Ronald H. Micheels and Don J. Lee, both of which are hereby fully incorporated by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. Copyright 2015 Innovative Science Tools, Inc.

BACKGROUND

Field of Technology

This disclosure relates to a light source, and more specifically to a near-infrared light source for use in near infrared transmission and reflection spectroscopy.

Background

Optical transmission and reflection spectroscopy in the short wavelength near-infrared range of 700-1050 nm has been used extensively in the past for important applications including identification of solid, powdered, and liquid materials and compounds, and quantification of the concentration of specific chemical compounds in solids, powders, and liquids. Spectroscopic analysis in the short wavelength near-infrared range is based on molecular vibrational overtone absorptions and light scattering effects in the 700-1050 nm wavelength range. The standard light source that is used for both reflection and transmission sampling modes in most of the near-infrared spectrometer systems that operate in the 700-1050 nm range is the tungsten-halogen lamp, which emits over a very broad wavelength range of about 350-3,000 nm.

Single crystal $Ti^{+3}$-Sapphire circular and rectangular cross-seciont rods and disks have been used as a broadly tunable laser medium. This material, which emits photoluminescence in the 600-1050 nm range and absorbs light from 400-620 nm, with 90% of the peak absorption within the range of 465-510 nm, has a high photoluminescent quantum efficiency in the range of 0.8 to 0.86. The excitation spectrum for Ti-Sapphire is expected to be very close to that of the absorption spectrum based on reported excitation and absorption spectra for ruby ($Cr^{+3}$ doped Sapphire). Examples of other types of solid state broad-band light sources used for optical spectroscopy and microscopy include: white LEDs, and laser based nonlinear plasma solid state sources, and nonlinear photonic crystal fiber based continuum lasers. With the exception of the white LED, which does not emit at wavelengths longer than 700 nm, these other broad band solid state light sources are not always suitable due to size and expense.

U.S. Pat. No. 6,836,502 (Canady et al., Dec. 28, 2004) describes a design for a broadband near-infrared light source for spectroscopy applications that consists of a LED excitation source together with a phosphor element based on either a CdS semiconductor crystal or polycrystal, or one or more fluorescent organic dyes dissolved in a clear polymer block, or one or more sizes of fluorescent quantum dots embedded in a clear polymer block. These three phosphor element design options have some drawbacks. Although CdS has a broad luminescence emission spectrum that covers a near-infrared wavelength range, it has been reported to have low photoluminescence quantum efficiencies of 0.22, with an even lower quantum efficiency implied from reported temperature dependence of photoluminescence between room temperature and low temperatures. Phosphor elements based on organic dyes have problems with photochemical degradation and also from reabsorption of luminescence due to insufficient separation between the peak absorbance wavelengths and the emission wavelength range for the dyes that emit at the longer wavelengths in the 850-1050 nm range. The organic fluorescent dyes only emit light in limited width wavelength bands of about 100 to 150 nm, which requires a mixture of several dyes to cover the desired 350 nm range of 700-1050 nm. Disadvantages of quantum dots include a very high material price, and also the close proximity of the absorption bands to the emission bands, which leads to reabsorption of luminescent emission light. Such reabsorption results in lowering of the effective quantum efficiency. Like the organic dyes, quantum dots have limited spectral emission bands on the order of about 100-150 nm which requires a mixture of several sizes of quantum dots to cover desired the 700-1050 nm range.

BRIEF SUMMARY

A light source for near-infrared transmission and reflection spectroscopy can be constructed from a combination of a high power blue or blue-green light emitting diode (LED) and a phosphor element based on an inorganic material. The phosphor element absorbs the blue or blue-green LED light and, in response to the LED excitation, emits luminescence in the 700-1050 nm range or at least the 700-1000 nm range. One possible material that can be used for such a near-infrared emitting phosphor element is a single crystal rod of $Ti^{+3}$ doped Sapphire, where the rod can be of circular or rectangular cross section. An alternative near-infrared emitting phosphor material is a round or rectangular shaped disk consisting of a composite of $Ti^{+3}$ doped Sapphire powder embedded in a clear optical epoxy or silicone encapsulant. Such a combination of a blue LED for excitation of a phosphor element that emits in a broad wavelength band has been widely used in white LEDs where the emission is in the 400-700 nm range. The LED plus inorganic phosphor based near-infrared light source has substantial advantages over a tungsten halogen source for field portable near-infrared transmission and reflection spectroscopy:

1. increased electrical to light conversion efficiency resulting in longer battery life when used in portable/handheld spectroscopic analyzer applications
2. longer life of the emitting element (approximately 25,000 hours for Ti-Sapphire source vs. 2,000 hours for tungsten halogen)

3. resistance to failure from exposure to mechanical shock
4. ability to be modulated at 100% modulation amplitude at frequencies up to about 10 kHz which permits phase sensitive detection processing for removal of sunlight and roomlight interference
5. no need for a cooling fan, which is normally required with tungsten-halogen lamps, allowing for easier incorporation into a waterproof package desirable for a ruggedized handheld spectroscopic analyzer.

The LED plus Ti-Sapphire phosphor near-infrared light source also has applications as a light source for optical microscopy. These applications in microscopy include use with samples stained with near-infrared absorbing and near-infrared emitting fluorescent dyes.

The photoluminescent material Ti-Sapphire has excellent potential as a solid-state near-infrared light source because of the following factors: 1) high quantum efficiency, 2) photoluminescence emission range of 600-1050 nm, and 3) peak absorption that coincides with the emission band of blue LEDs that are available with small LED chip diameters of about 1 mm and high optical emission power levels of about 0.5 W. The Ti-Sapphire light source can be fabricated with a small output diameter of about 1-3 mm which is very well suited for efficient coupling to fiberoptic bundles that are used for illumination in bifurcated fiber-optic reflection probes that are often employed for near-infrared spectroscopy in the reflection mode.

BRIEF DESCRIPTION OF THE DRAWINGS

In the drawings, closely related figures and items have the same number but different alphabetic suffixes. Processes, states, statuses, and databases are named for their respective functions.

DETAILED DESCRIPTION, INCLUDING THE PREFERRED EMBODIMENT

In the following detailed description, reference is made to the accompanying drawings which form a part hereof, and in which are shown, by way of illustration, specific embodiments in which the invention may be practiced. It is to be understood that other embodiments may be used, and structural changes may be made without departing from the scope of the present invention.

Reflection Spectral Measurements

Figure 1:
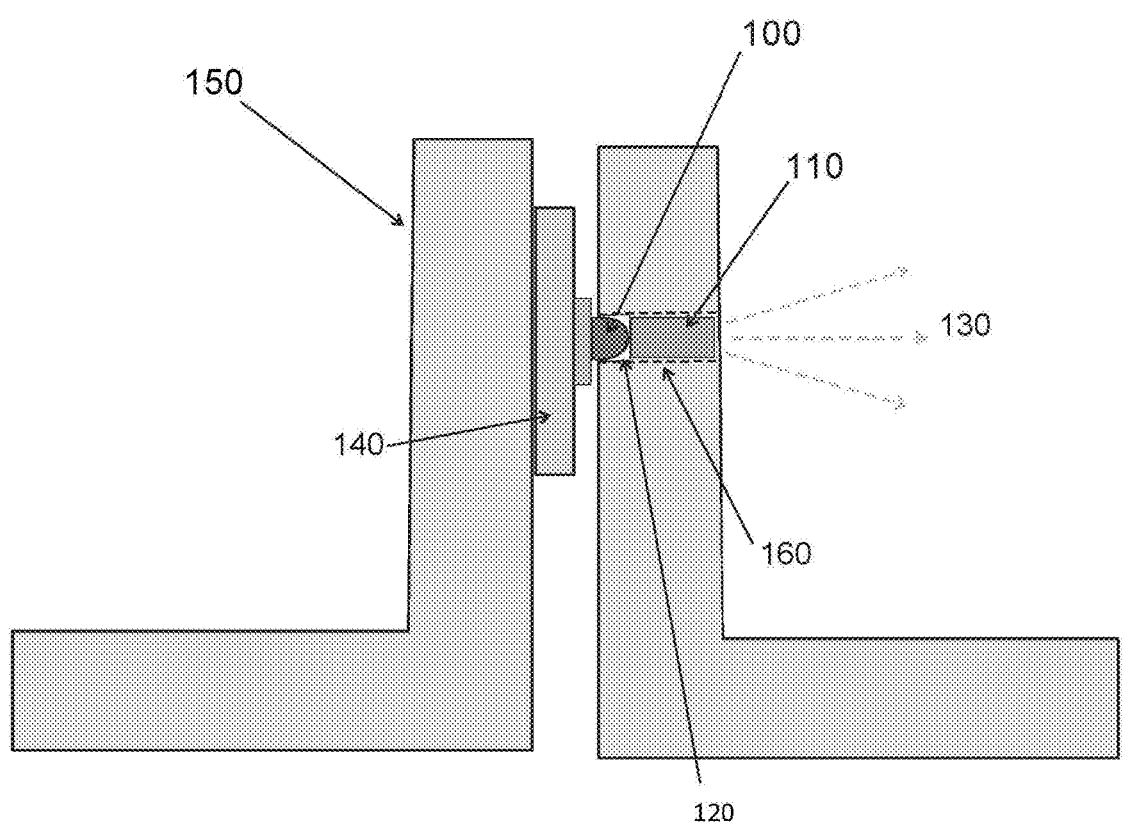
FIG. 1 is a diagram of a blue LED excited Ti-Sapphire rod near-infrared light source.

A design of the Ti-Sapphire based light source, as shown in FIG. 1, includes an excitation light source consisting of high power (0.2-1.0 Watt) blue or blue-green LED 100 with a center wavelength between 560 to 490 nm, with a molded-in plastic lens positioned against $Ti^{+3}$ doped sapphire laser rod 110, with small air space 120 between the LED lens and the Ti-Sapphire rod due to curvature of the lens. Optionally, the air space between the LED lens and the Ti-Sapphire rod may be filled with a clear optical encapsulant such as an optical epoxy or optical grade silicone encapsulant to reduce solid material/air interface optical reflection losses. The dashed arrows indicate the output light 130 emitted from this solid state light source. The LED may be mounted onto printed circuit board 140, with laminated aluminum heat-sink plate 150 on one side, providing electrical and thermal contacts to the LED. Aluminum mount 160 may include a drilled hole to contain the LED and Ti-Sapphire rod. The light source in this configuration may be coupled to an illumination fiber bundle for reflection spectroscopy or directly coupled to a solid or liquid phase sample for transmission mode spectroscopy. The concentration of $Ti^{+3}$ in the Sapphire rod should be in the range of 0.4-5%.

Figure 2:
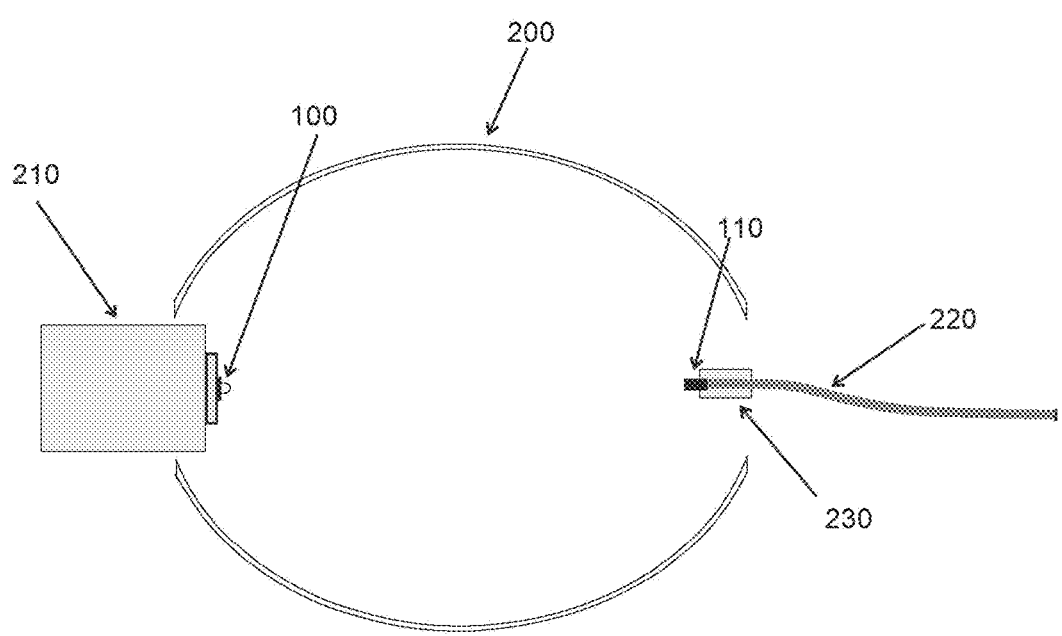
FIG. 2 is a diagram of an alternative optical configuration for coupling the light emitted from a blue LED to a Ti-Sapphire rod.

FIG. 2 shows an alternative optical configuration for coupling of the exciting LED emission to the Ti-Sapphire rod with an ellipsoidal reflector. High power blue LED 100 is positioned at one foci of ellipsoidal reflector 200, such as by mounting and positioning the LED on aluminum heatsink mount 210. Ti-Sapphire rod 110 is positioned at the opposite foci of the ellipsoidal reflector, and connects to illumination fiber-optic bundle 220, which may be positioned for connection through aluminum tube 230.

Figure 3:
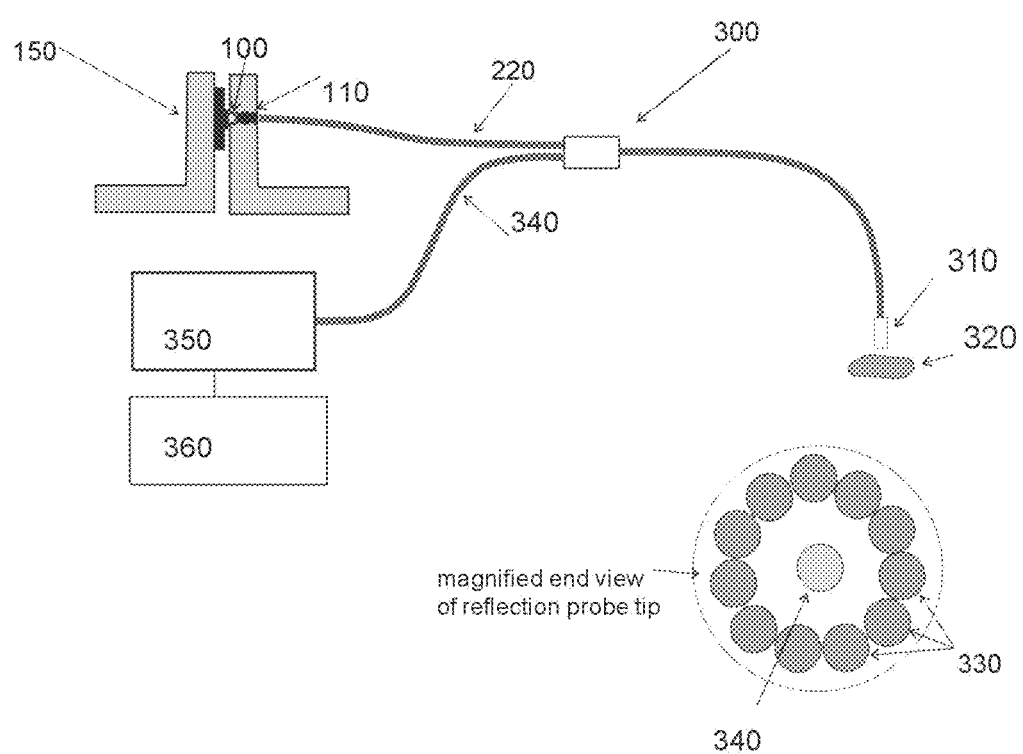
FIG. 3 is a diagram of application of the light source from FIG. 1 for reflectance spectroscopy.

As shown in FIG. 3, when the Ti-Sapphire light source is used for spectroscopic reflection measurements, the light source is coupled to illumination fiber bundle 220 that is part of bifurcated fiber-optic reflection probe 300, where reflection probe tip 310 couples to sample 320. Illumination fiber bundle 220 contains illumination optical fibers 330, which at tip 310 surround single receiving fiber 340. As an alternative to the illumination fiber bundle, a single illumination fiber may be used. Receiving fiber 340 delivers reflected light to spectrometer module 350. The spectrometer module may be a miniature diffraction grating spectrometer module with a Si-array detector that is used to measure the reflection spectra and is connected to computer 360 for control of spectral collection and processing. While the light source from FIG. 1 is shown in FIG. 3, both of the light source designs in FIGS. 1 and 2 can be similarly used as the illumination source for a hand held or portable NIR spectrometer system that employs a Si array detector microspectrometer module to measure near-infrared spectra.

Transmission Spectral Measurements

Figure 4:
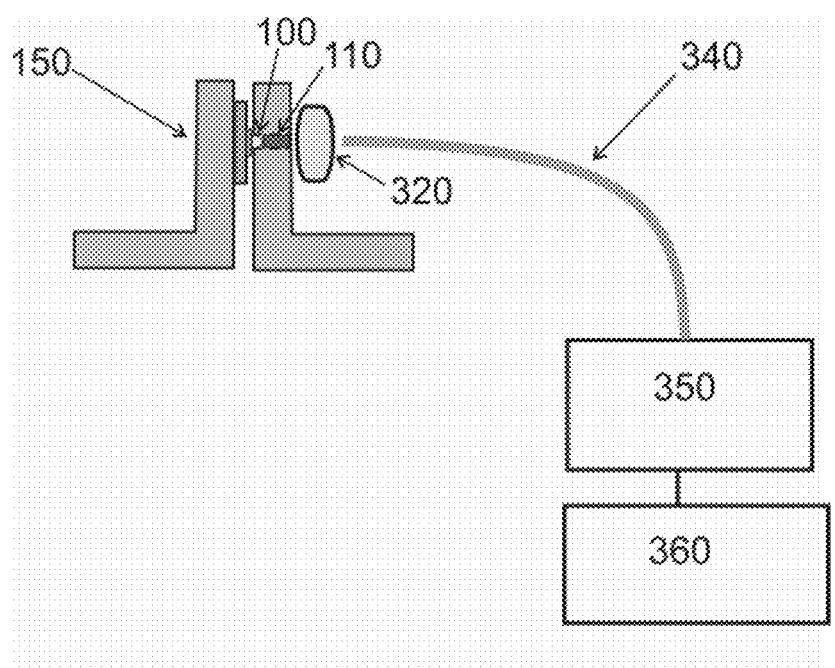
FIG. 4 is a diagram of application of the light source from FIG. 1 for transmission spectroscopy.
Figure 5:
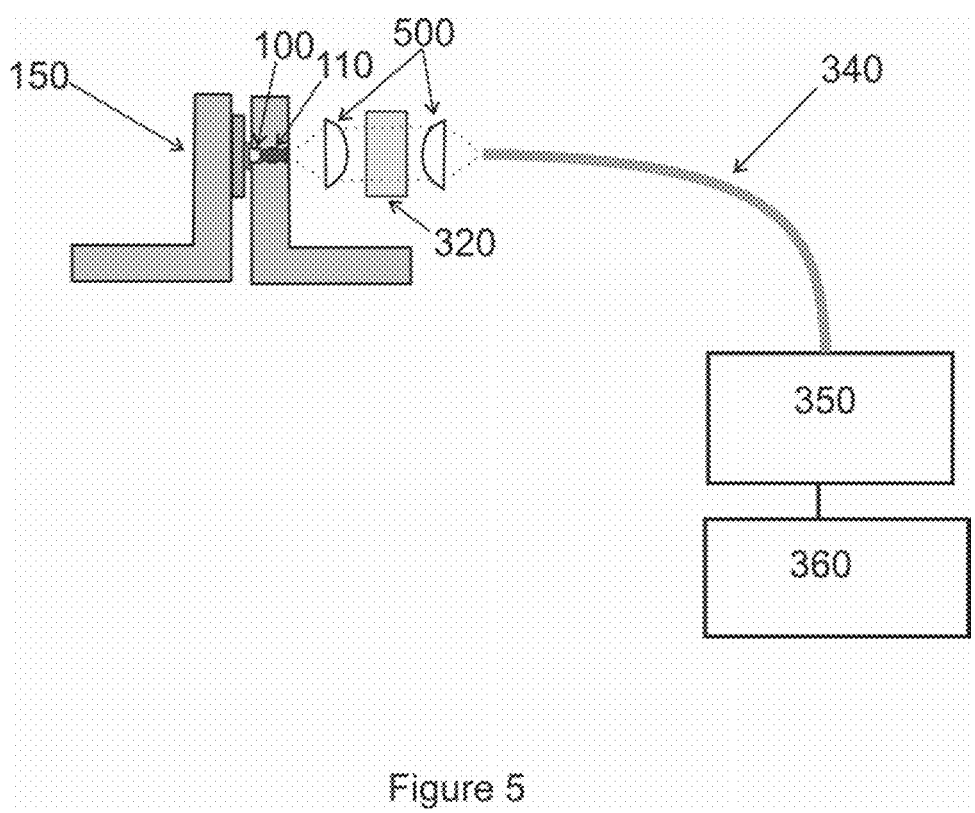
FIG. 5 shows a variation of FIG. 4 for transmission sampling of a transparent sample.

When the Ti-Sapphire light source is used for transmission spectroscopic measurements, the light source is either directly coupled to the sample, as shown in FIG. 4, or coupled to the sample through a collimating lens for transparent samples as shown in FIG. 5. As shown in FIG. 4, the sample may be positioned immediately after the Ti-Sapphire rod, and followed by receiving fiber 340 to direct transmitted light to the spectrometer module. With this latter configuration, no collimating or focusing optical elements are needed past the laser rod. In FIG. 5, the sample is located between a pair of lenses 500. First, a collimating lens directs light from the light source to the sample, and then a focusing lens focuses the collimated light that is transmitted through the sample onto receiving fiber 340 that connects to spectrometer module optical input. Alternatively, for transparent samples, a single lens can be used instead of the separate collimating and focusing lenses in FIG. 5, where the single lens (placed either before or after the sample) is used both to collect the light emitted from the Ti-Sapphire source and to send it through the sample as a converging optical beam, and then onto the spectrometer receiving fiber.

Ti-Sapphire Near-Infrared Phosphor Material and LED Light Source

Phosphor Consisting of Single Piece of Ti-Sapphire Material

In the simplest configuration, the Ti-Sapphire phosphor material for the solid-state near-infrared light source is in form of a single crystal or polycrystalline rod or disk. This is the configuration shown in FIGS. 1-5, where the LED has a molded-in lens and there is an air gap between the LED lens and the Ti-Sapphire rod. There are several other possible phosphor configurations that are described in the following sections.

Figure 6:
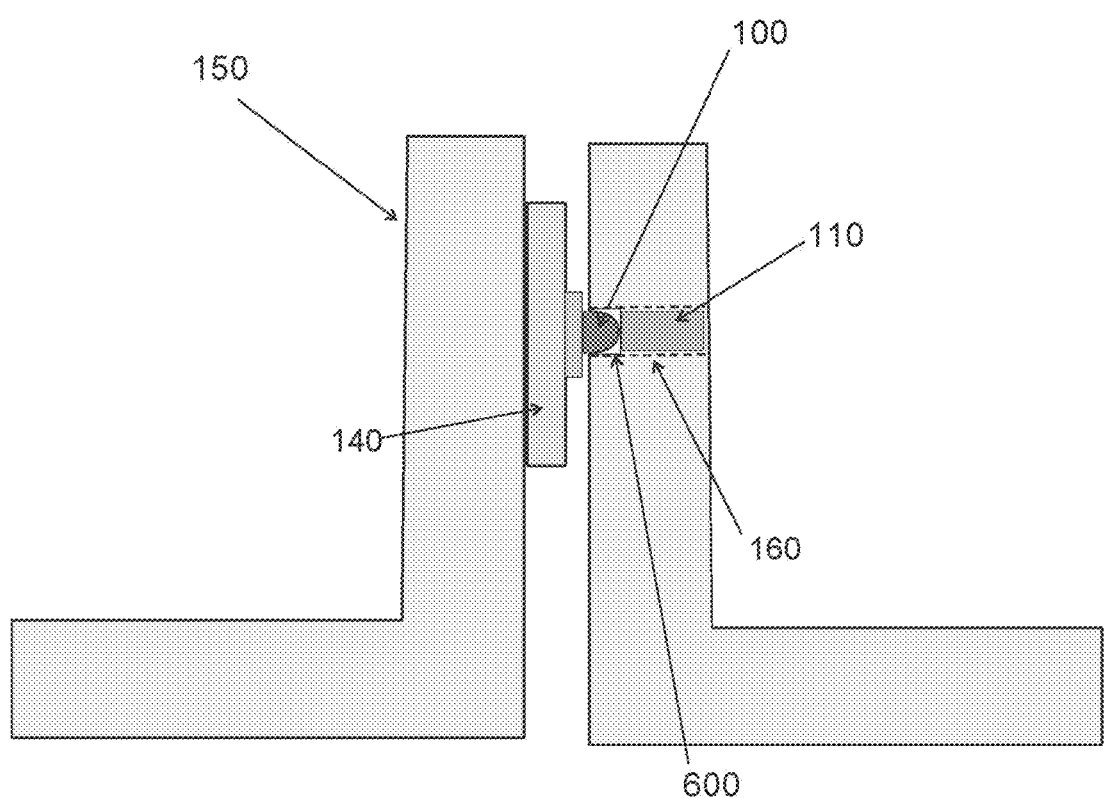
FIG. 6 shows a variation of FIG. 1 adding a clear optical encapsulant layer.

An LED with a Molded-in Lens and the Air Gap between the LED Lens and the Ti-Sapphire Rod Filled with a Clear Optical Encapsulant Referring to FIG. 6, optical encapsulant 600, such as an optical grade epoxy or silicone encapsulant, fills in the air gap between the high power blue or blue-green LED molded-in lens (typically a surface mount high power LED package) and the Ti-Sapphire rod. This configuration produces a higher efficiency of coupling of the LED light to the Ti-Sapphire rod than the configuration configurations without the optical encapsulant, such as the configuration shown in FIG. 1. The higher LED light coupling efficiency is the result of a reduction of the reflection losses from the air gap after the gap is filled with an encapsulant material having an index refraction more closely matching that of the LED encapsulant material and Sapphire than air.

Figure 7:
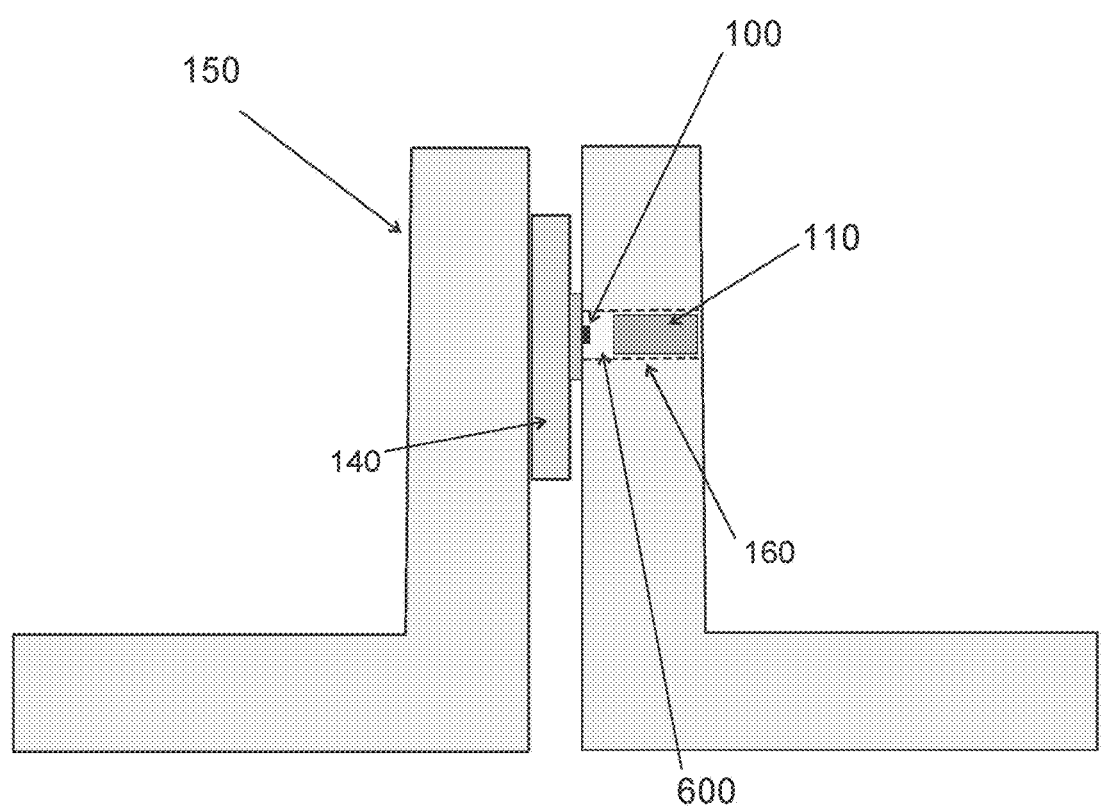
FIG. 7 shows a variation of FIG. 6 using a mounted LED chip without a lens.

Ti-Sapphire Light Source Configuration with an LED Chip Without a Lens and the Air Gap Filled with an Optical Encapsulant Referring to FIG. 7, an alternative configuration of the Ti-Sapphire light source has a LED without a molded in lens and the space between the LED chip and the Ti-Sapphire rod is filled in with a clear optical encapsulant. Some surface mount packaged LEDs have no molded-in lens and have a flat optical encapsulant layer over the LED chip, and in this case a second optical encapsulant layer may be added, on top of the optical encapsulant that is part of the original LED package, in order to fill the space between the LED structure and the Ti-Sapphire rod. The LED chip also can be custom encapsulated with a single optical encapsulant layer between the LED chip and the Ti-Sapphire rod.

Embodiments with the Phosphor Material in Form of Powdered Ti-Sapphire Together with a Transparent Optical Encapsulant/Binder Material Deposited on Top of LED Die (Similar to Typical White LED Design).

Figure 8:
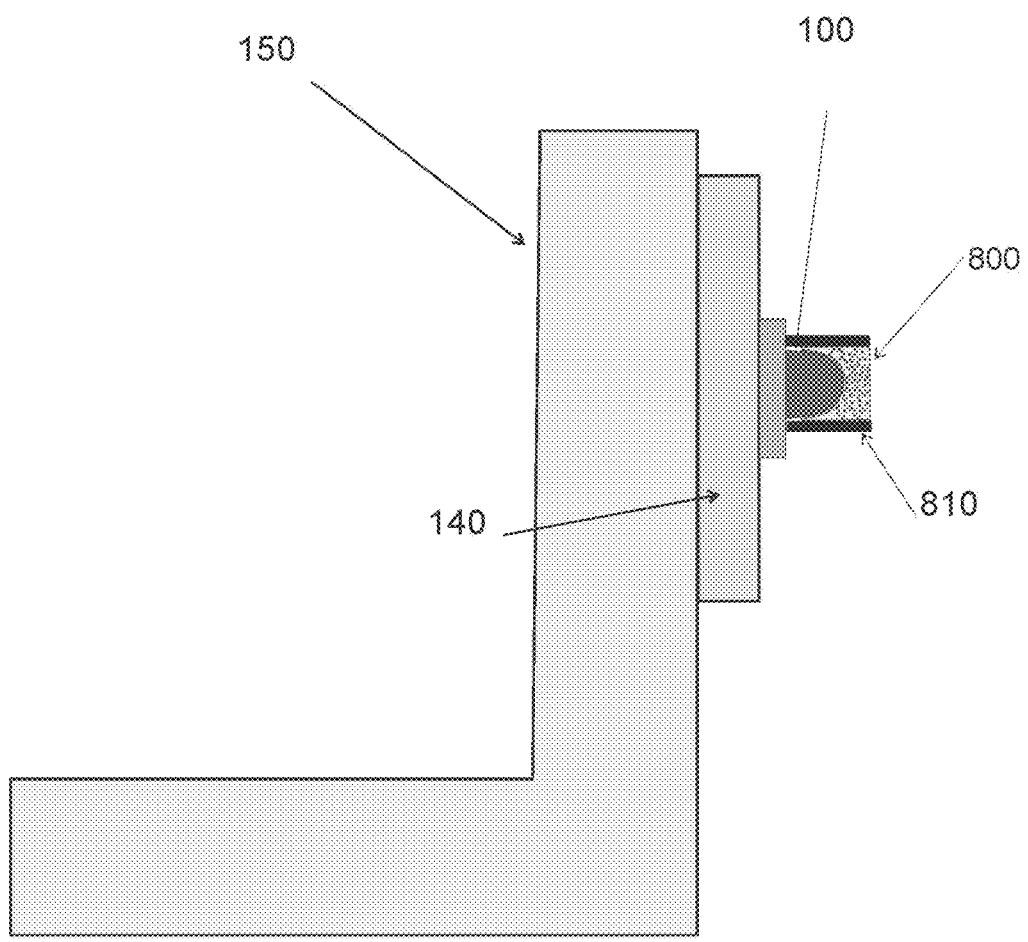
FIG. 8 shows a variation of FIG. 1 replacing the Ti-Sapphire rod with Ti-Sapphire powder embedded in a clear optical encapsulant.
Figure 9:
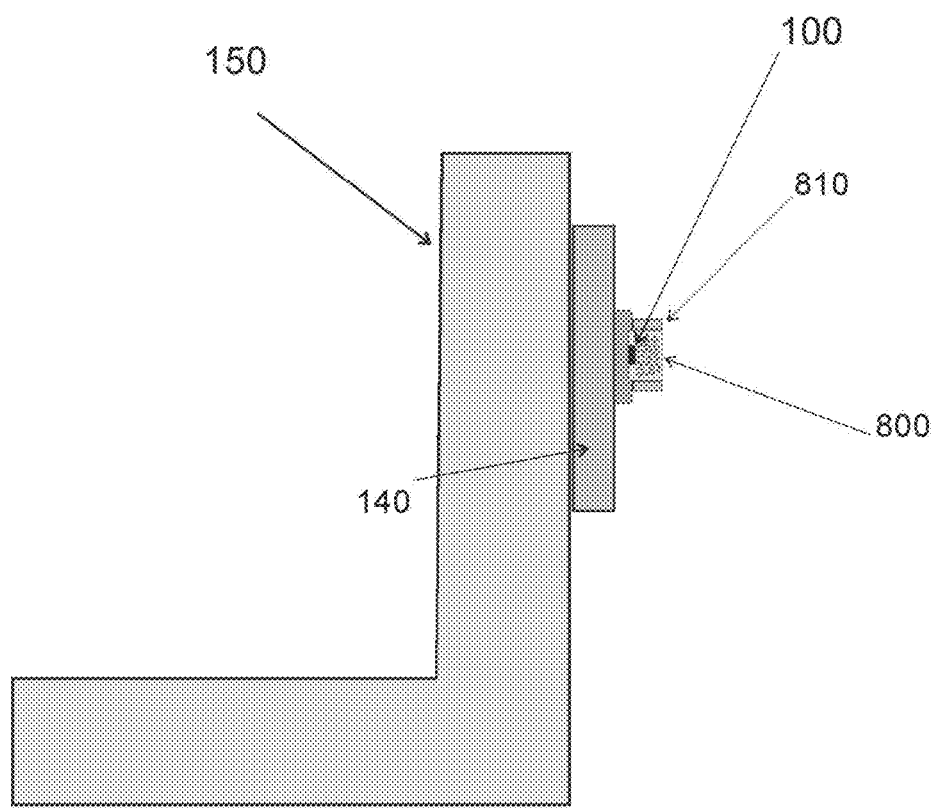
FIG. 9 shows a variation of FIG. 8 using a mounted LED chip without a molded-in lens.

Referring to FIG. 8, another alternative configuration for a near-infrared light source based on Ti-Sapphire is to embed uniformly dispersed Ti-Sapphire powder in a layer of clear optical encapsulant material 800 such as optical grade epoxy or silicone. The optical encapsulant layer containing the Ti-Sapphire powder can be applied on top of the blue or blue-green LED molded-in lens, as shown in FIG. 8. Aluminum or aluminum-coated tube 810 may be used as a border container for the encapsulant layer. Aluminum is a preferred material for the border container because of the high reflectivity of aluminum in the near-infrared and the low cost of the material. Gold coated stainless steel or gold coated aluminum may also be used for the border container material, and has slightly higher reflectivity than aluminum, but would have a higher cost. Referring also to FIG. 9, the encapsulant layer with embedded Ti-Sapphire powder can also be used on top of the flat optical encapsulant layer in the case of a surface mount LED package without a lens or to directly encapsulate a bare LED chip in the case of custom encapsulation.

Other Embodiments

An alternative embodiment is to replace the LED optical excitation light source with a blue diode laser diode emitting at about 470 nm or a near-infrared diode laser pumped frequency doubled Nd-YAG laser emitting at 532 nm.

Another alternative embodiment is to use lenses or concave mirrors or a combination of lenses together with concave mirrors to couple the light from the LED excitation source to the Ti-Sapphire rod.

Another alternative embodiment is to use lenses or concave mirrors or a combination of a lens or lenses with a concave mirror or mirrors to couple the output light from the Ti-Sapphire rod to an illumination optical fiber bundle, or to the sample in the case of transmission sampling.

Another alternative embodiment is to add a second luminescent material to the primary NIR phosphor material, where the primary phosphor element is in the form of a powdered phosphor element embedded in a clear optical encapsulant. For example, such a two component near-infrared phosphor element may be a mixture of Ti-Sapphire powder plus a second powder embedded in a clear optical encapsulant, where the second powder consists of or a quantum dot material such as: PbS, PbS(core)/CdSe(shell), CdS, CdSe, Si, Au, or other photoluminescent quantum dot materials with an appropriate size range to emit within the wavelength range of 930-1050 nm. The second luminescent material enhances the emission of the solid state light source in the 920-1100 nm range, where the emission from Ti-Sapphire is weaker. Alternatively, the second phosphor powder may be a powdered form of another transition metal or rare earth element doped crystalline material, to provide a combined phosphor material with greater emission intensity in the 920-1100 nm spectral range than Ti-Sapphire alone. As another alternative, a layer of a second luminescent material, such as PbS quantum dots, in the form of a layer of powder embedded in a clear optical encapsulant, may be added to the end of a single crystal rod of Ti-Sapphire. More than one additional luminescent powder may also be used.

Figure 10:
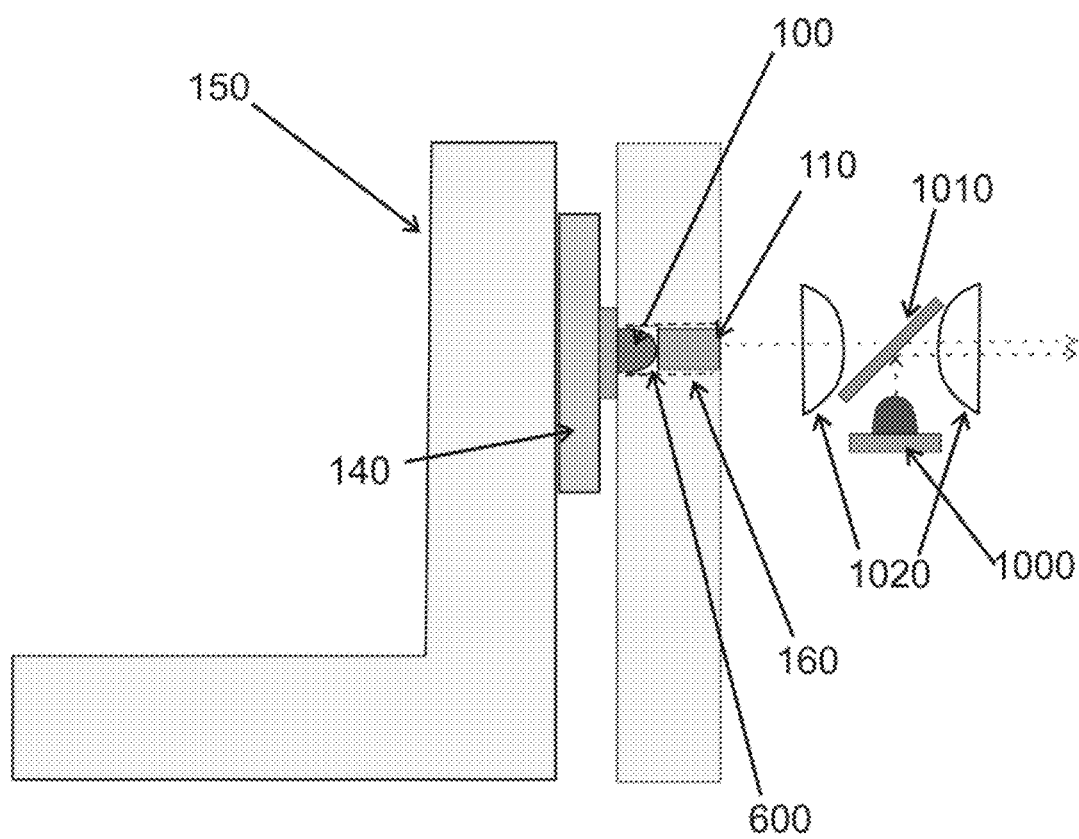
FIG. 10 shows a variation of FIG. 6 combining the light output of from the blue LED/Ti-Sapphire light source with a near-infrared LED to achieve more light intensity in the 920-1100 nm range.

Referring to FIG. 10, another alternative embodiment combines the optical emission from the blue LED excited Ti-Sapphire element (either Ti-Sapphire rod or Ti-Sapphire powder embedded in optical encapsulant) with the optical emission from high power near-infrared LED 1000 with center emission wavelength of the LED in the range of 920 to 1050 nm to provide more optical power in the 920-1100 nm range where the Ti-Sapphire emission is weaker. The light from the Blue LED/Ti-Sapphire element may be combined with the light from the near-infrared LED using dichroic beamsplitter 1010. The dichroic beamsplitter transmits light from one source at one wavelength range and reflects light at 45 degrees to the normal incidence for another complimentary wavelength range, where the transmitted wavelength range is 700-940 nm and the reflected range is 950-1050 nm. Using a dichroic beamsplitter with these latter transmitted and reflected wavelength ranges reversed, together with a reversal of the positions of the near-infrared LED and the Ti-Sapphire light source, is an alternative option. It is preferred to include a pair of plano-convex lenses 1020 to relay the combined light to either the sample or a fiber-optic bundle that is part of a bifurcated fiber-optic reflection probe. As shown in FIG. 10, the dichroic beamsplitter may be located in-between the two plano-convex lenses in the preferred optical configuration. Optionally, a third external convex lens may follow the near-infrared LED or be bonded to this near-infrared LED with a clear optical encapsulant to better collimate the light emitted by the near-infrared LED. Such an additional lens may be located in the near-infrared LED beam path between the LED and the second lens before the dichroic beamsplitter.

Another alternative embodiment combines the optical emission of the blue LED excited Ti-Sapphire element with the emission from a white LED using a dichroic beamsplitter to provide a solid state light source covering the 400-1050 nm spectral range. This design follows the design shown in FIG. 10, with near-infrared LED 1000 replaced with a white LED. The dichroic beamsplitter has the appropriate construction to transmit light in the 710-1050 nm range from the Ti-Sapphire source and reflects light in the 400-700 nm range from the white LED source. Using a dichroic beamsplitter with these latter transmitted and reflected wavelength ranges reversed, together with a reversal of the positions of the white LED and the Ti-Sapphire light source, is an alternative option. A combined visible/near-infrared solid state light source may be useful for identification of materials that have important spectral features in both visible and near-infrared wavelength ranges such as minerals and paint or ink pigments.

Figure 11:
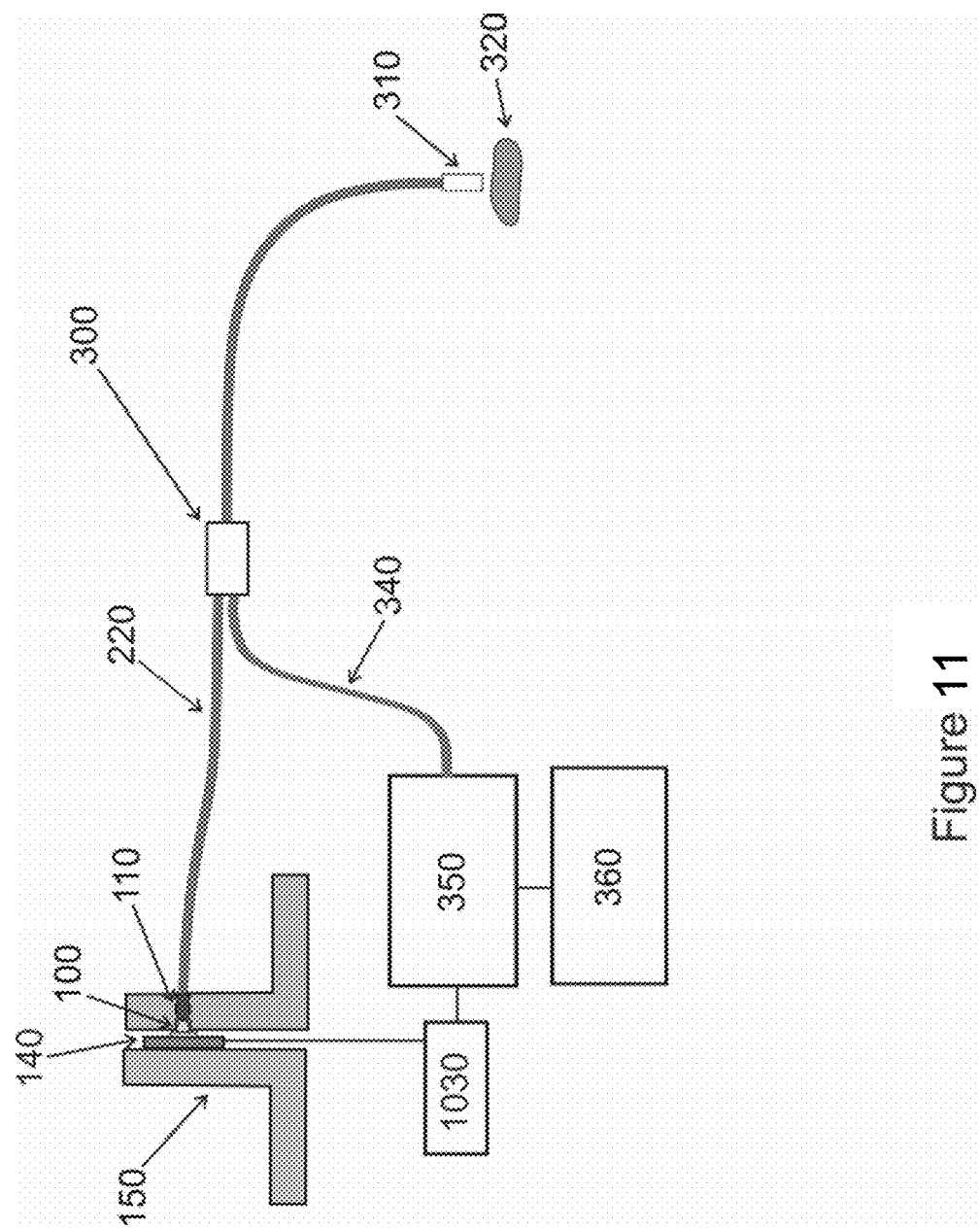
FIG. 11 shows a diagram of a near-infrared optical spectrometer system with an embodiment of the T-Sapphire near-infrared light source that is square or sine-wave modulated to allow removal of interfering sunlight or room-light that might enter the optical spectrometer without passing through or interacting with the sample being measured.

A variation applicable to all alternative embodiments includes square-wave or sine-wave modulation of the blue or blue-green LED driving current. In this design and method the spectral collection uses phase sensitive detection signal processing (also referred to as lock-in amplification) together with the square or sine-wave modulated Ti-Sapphire light source to allow elimination of interference in the measured spectra from sunlight or room lights that enters the spectrometer optical input. The phase sensitive signal processing means is synchronized with the square-wave or sine-wave modulation of the Ti-Sapphire based light source. The modulation frequency is in the range of 10 Hz-10 KHz and the amplitude modulation of the light source is between 90-100%. Interference from sunlight or room lights can be a problem in measuring reflection spectra with a fiber-optic reflection probe or other means for reflection sampling when samples with very non-planar surfaces are measured or when a significant sample standoff distance is required. In FIG. 11, electronic modulation circuit module 1030 has a first electrical output that connects to and drives the blue LED excitation light source with square or sine-wave modulation, and a second output for triggering or synchronizing the spectral collection electronics of the optical spectrometer module to the modulation waveform. The modulation of the near-infrared light emitted by the T-Sapphire phosphor element follows the blue LED modulation for modulation frequencies up to at least 1,000 Hz. The removal of interfering sunlight or room light from near-infrared spectra collected by spectrometer module 350 can be achieved by modulating the near-infrared light source with square or sine-wave modulation and then processing the resulting signal in the spectrometer detection system using lock-in amplification, which is also referred to as phase sensitive detection. One way to effectively achieve lock-in amplification with an optical spectrometer having a photodiode, CCD, or CMOS array detector is to gate the collection of the detector array data from the spectrometer detector array in synchronous with the on/off square wave modulation of the near-infrared light source. In this signal processing scheme, averaged spectra are collected in two arrays, with one array corresponding to the periodic modulation intervals occurring when the near-infrared light source is on, and a second array corresponding to modulation cycle when the near-infrared light source is off. When the two spectral data arrays corresponding to the light source on and light source off are subtracted, the resulting spectrum has contributions removed that originate from non-synchronous light sources such as sunlight or room-light.

Other Inorganic Phosphor Materials

Other crystalline photoluminescent inorganic materials that emit over a wide wavelength band in NIR may be used instead of $Ti^{3+}$-sapphire. Examples of other possible photoluminescent inorganic crystalline materials include: $Cr^{+3}$-

LiSrAlF$_6$ (emits in 750-950 nm range) and Ti$^{+3}$BeAl$_2$O$_4$ (emits in 700-900 nm range).

Experimental Results

With the light source and optics configurations as discussed above, the range of applicable samples, sample holders, spectrometer modules, and computer or microprocessor to control spectral data acquisition, analysis, and processing are as detailed U.S. Pat. No. 8,859,969 and U.S. Pat. Pub. No. 2013/0265568. The diffuser shown in FIG. 23 of the co-pending applications is not used for coupling the Ti-Sapphire/LED light source to the illumination fiber bundle of the fiber-optic probe. The results of using the Ti-Sapphire light source in such systems, such as shown in FIGS. 3-5, are discussed below, as well as comparisons between the Ti-Sapphire light source and a tungsten-halogen light source.

Ti-Sapphire Absorbance Spectrum Together with Blue LED Emission Spectrum

Figure 12:
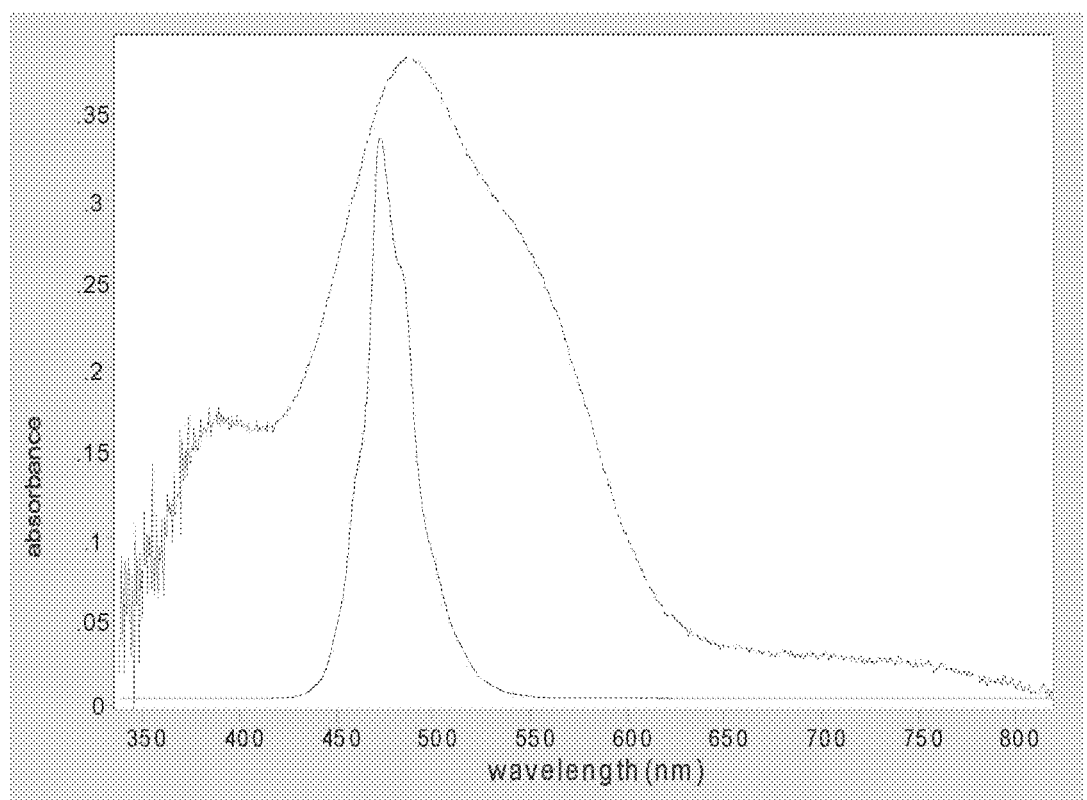
FIG. 12 shows a graph comparing the absorbance spectrum of a Ti-Sapphire rod with approximately 0.5% $Ti^{+3}$ concentration against the emission spectrum of a Cree high power blue LED.

The absorbance spectrum (transmission spectrum in absorbance units) of a Ti$^{+3}$-Sapphire rod with a Ti$^{+3}$ concentration of about 0.5% by weight and a rod length of 4 mm and diameter of 3 mm) is shown as the upper line in FIG. 12. The lower line shows the emission spectrum of a Cree high power blue LED with peak emission at about 475 nm, which can be seen as being a good match to the wavelength region of 465-510 nm where the Ti-Sapphire absorbance is within 90% of its peak absorbance. For the 0.5% Ti$^{+3}$ concentration, the absorbance of a 4 mm long Ti-Sapphire rod at the peak blue LED wavelength is about 0.35, which corresponds to 55% of the LED light being absorbed by the Ti-Sapphire rod.

Figure 13:
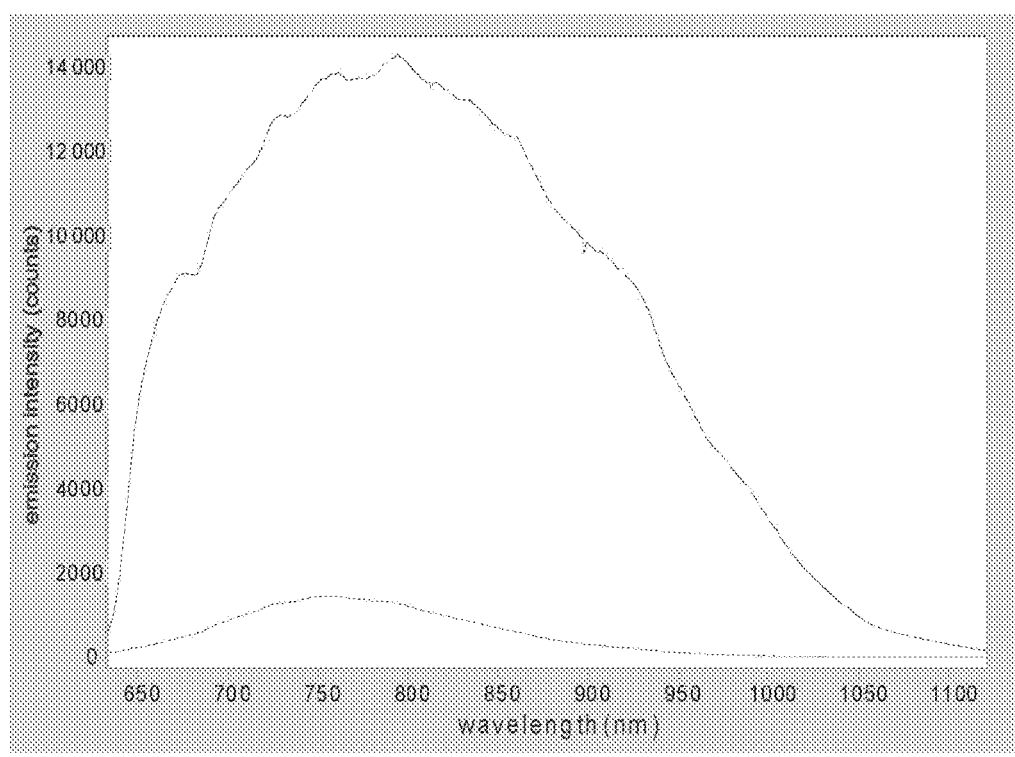
FIG. 13 shows a graph comparing the short wavelength near-infrared emission spectra of a commercial spectroscopic tungsten halogen light source with that of a blue LED excited Ti-Sapphire light source.
Figure 14:
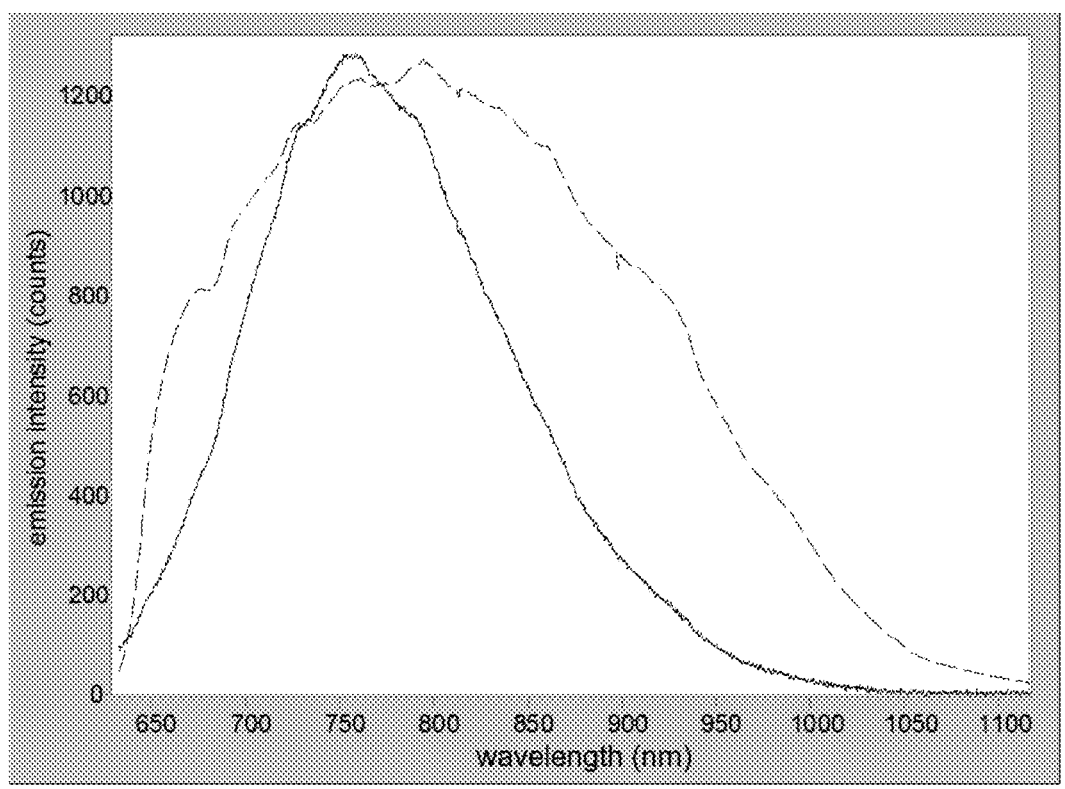
FIG. 14 shows a modification of FIG. 13 with the Ti-Sapphire source spectrum rescaled to have the same peak intensity as the tungsten halogen source.

Near-Infrared Emission Spectrum of the Blue LED Excited Ti-Sapphire Laser Rod, and Comparison with Tungsten Halogen Lamp The emission spectrum from a Ti-Sapphire rod, 4 mm in length, that was excited with a high power blue LED (475 nm) and directed into an illumination fiber bundle that is part of a bifurcated fiber-optic reflection probe, was measured as the reflected light spectrum from a white Spectralon block. The light from the illumination fiber bundle reflected off of the Spectralon block and was picked up by a single 400 μm optic fiber at the tip of the bifurcated fiber-optic reflection probe. The design of the fiber-optic reflection probe is as shown in FIG. 3, except using thirteen fibers in the illumination fiber bundle. FIGS. 13 and 14 show the emission spectrum of the Ti-Sapphire source that diffusely reflects from the Spectralon block, and also the emission spectrum (reflected from the Spectralon block) of a commercial fiber-optic tungsten-halogen light source that was designed for use with miniature optical spectrometers having fiber-optic inputs. The spectrum measured for the tungsten-halogen source was taken with the same bifurcated fiber-optic reflection probe and Spectralon block used for the Ti-Sapphire source spectrum. The emitted light from the tungsten-halogen source was filtered with a long pass optical filter that limits transmitted light to wavelengths longer than 645 nm to avoid saturation of the spectrometer with strong shorter wavelength emission in the 350-645 nm range. In FIG. 13, where the emission spectra of both the Ti-Sapphire light source and the tungsten-halogen light sources are plotted on the same emission intensity scale (after transmission through the illumination fiber bundle), it can be seen that the tungsten-halogen light source (upper spectrum) peak near-infrared emission intensity is about 10 times that of the Ti-Sapphire near-infrared light source (lower spectrum) peak. The tungsten halogen source used 15 W of electrical power while the blue LED excited Ti-Sapphire light source only used 2.5 W. FIG. 14 shows the same results with the Ti-Sapphire source spectrum rescaled to have the same peak intensity as the tungsten halogen source, where the dashed line spectrum is the tungsten halogen source and the solid line spectrum is the Ti-Sapphire source. These results show that both light sources cover a similar wavelength range, with the Ti-Sapphire emission spectrum similar to that of the tungsten-halogen lamp in the 700-950 nm range but weaker in the 950-1100 nm range. The design of the Ti-Sapphire light source used for the emission spectral measurements plotted in FIGS. 13 and 14 is as shown in FIG. 1 and more optimal designs such as those shown in FIGS. 6 and 7, or with the use of a Ti-Sapphire rod with a longer length or higher Ti$^{+3}$ concentration, would lead to substantial increases in the emission intensity of the Ti-Sapphire light source.

Figure 15:
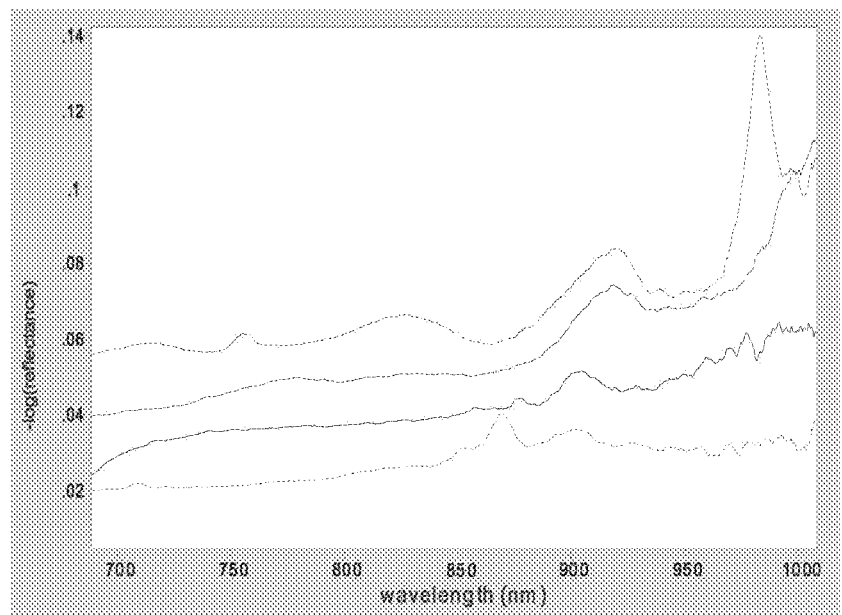
FIG. 15 shows a graph of near-infrared reflection spectra of four drug ingredient powders, each separately contained in clear polyethylene bags, and measured using a ultra-miniature diffraction grating spectrometer, a fiber-optic reflection probe, and a blue LED excited Ti-sapphire light source.
Figure 16:
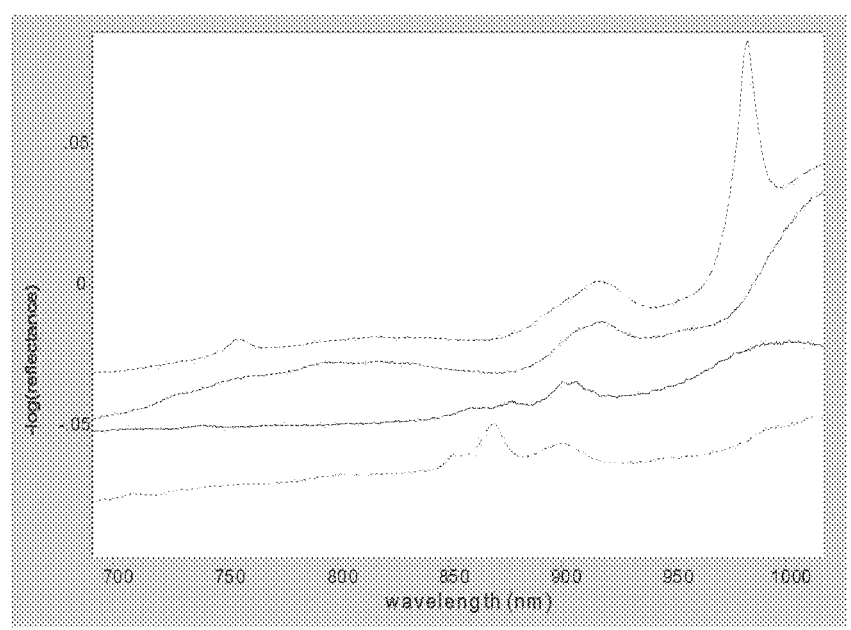
FIG. 16 shows a graph of reflection spectra of the same four drug ingredient powders shown in FIG. 15 using a commercial tungsten halogen fiber-optic light source that uses 15 W of electrical power, together with the same spectrometer used for the FIG. 15 spectra.

Reflection Spectra Measured with Ti-Sapphire and Tungsten Halogen Light Sources for Powdered Samples FIGS. 15 and 16 show near-infrared reflection spectra of 4 different powdered compounds contained in small 5×8 cm clear polyethylene plastic bags that were measured with both the Ti-Sapphire and tungsten-halogen light sources with a bifurcated fiber-optic reflection probe and a ultra-miniature optical spectrometer module. FIG. 15 shows the measurements of these powder spectra with the Ti-Sapphire light source configured as shown in FIG. 3. A spectral collection time of 10 seconds was used and the blue LED driving current was 550 mA resulting in 1.9 W power usage. The spectrum in FIG. 15 was processed with a 21 point Savitsky-Golay smoothing routine. FIG. 16 shows the measurements with the same setup but with a 15 W tungsten-halogen light source, and again using a 10 second collection time. The fiber-optic reflection probe used for the spectral measurements in both FIGS. 15 and 16 included a 2 mm thick anti-reflection coated glass window to protect the probe tip, which also provided a small stand-off distance from the sample surface. A Spectralon block was employed to record light source reference reflectance spectra that is used to produce the −log(reflectance) spectra plotted.

In both FIGS. 15 and 16, the top spectrum is sucrose, the second spectrum from the top is glucose, the third spectrum is acetaminophen, and the bottom spectrum is amoxicillin. These compounds exhibit distinct spectral patterns that can easily be differentiated by eye or by standard multivariate calibration algorithms such as Partial Least Squares discriminate analysis or Principle Component Discriminant analysis. The spectral patterns shown in FIG. 15, as measured with the Ti-Sapphire near-infrared light source, have the same shape as those measured using the tungsten-halogen light source and shown in FIG. 16.

Near-Infrared Transmission Spectra of Drug Tablets Measured with the Ti-Sapphire and Tungsten-Halogen Light Sources The configuration shown in FIG. 4 was used to measure transmission spectra (plotted in absorbance units) of two different types of drug tablets with the Ti-Sapphire light source together with a ultra-miniature diffraction grating spectrometer module. Light source reference spectra were measured using a Spectralon (compressed and sintered Teflon powder) disk with a thickness of 4.5 mm in place of the tablet sample. The Spectralon disk produces about the same average optical attenuation from light scattering in the 700-1050 nm range as a typical drug tablet, but without any spectral features. The receiving optical fiber for the ultra-miniature spectrometer module was placed just after the tablet sample or the Spectralon disk for spectral measurement. Transmission spectra were also measured using a 15

W commercial fiber-optic tungsten halogen light source filtered with a 645 nm (50% cutoff point) longpass glass filter that transmits at wavelengths longer than about 640 nm and blocks ultraviolet and visible wavelength light. For the tungsten halogen spectra, the optical configuration illustrated in FIG. 4 was used, with the Ti-Sapphire source replaced with the 15 W tungsten halogen light source. The commercial 15 W tungsten-halogen fiber-optic light source couples light emitted by the tungsten filament to an SMA fiber optic connector using a convex focusing lens. The commercial fiber-optic tungsten halogen source used for the transmission mode spectral measurements was modified by replacing the focusing lens and SMA fiber-optic connector assembly with an external convex lens of slightly larger focal length and diameter to focus the tungsten-halogen light onto the front surface plane of the sample. This modification of the tungsten halogen source increased the light intensity level transmitted through the samples or the Spectralon disk by more than a factor 10.

Figure 17:
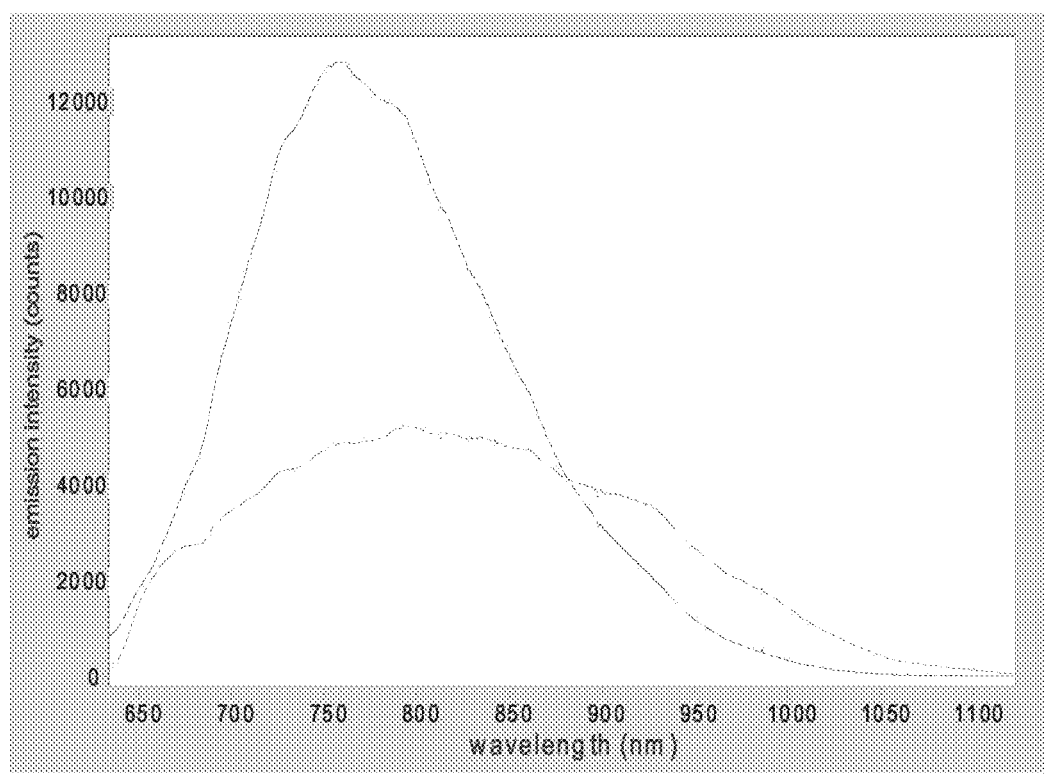
FIG. 17 shows a graph of the emission spectra measured through a 4.5 mm thick Spectralon disk for a blue LED excited Ti-Sapphire light source and a commercial 15 W tungsten halogen source, both plotted on the same vertical scale.

FIG. 17 shows a comparison of the emission spectrum of the blue LED excited Ti-Sapphire light source (upper spectrum) with that of the modified 15 W tungsten halogen source (lower spectrum). The emission spectra in FIG. 17 were measured using the optical arrangement shown in FIG. 4 with a 4.5 mm thick Spectralon disk as the sample, where the emission spectra were measured after transmission through the Spectralon disk. The Ti-Sapphire source has higher intensity in the 700-900 nm range while the tungsten-halogen source is stronger in the 900-1050 nm range. Spectral collection times of 9 seconds and 10 seconds were used respectively for the Ti-Sapphire source and the tungsten-halogen source.

Figure 18:
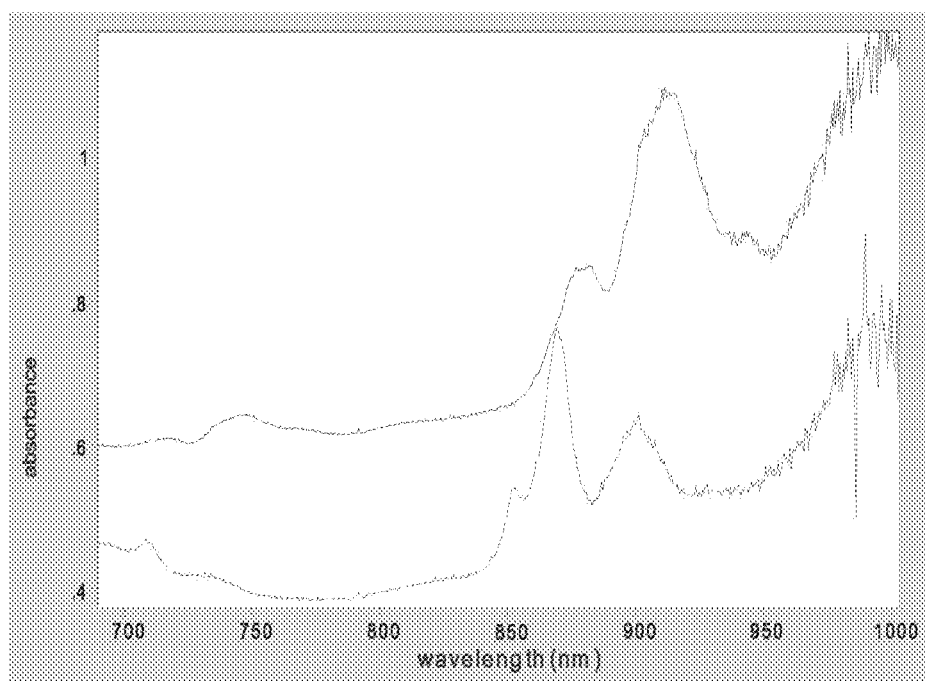
FIG. 18 shows a graph of near-infrared transmission spectrum (in absorbance units) of Tylenol and Motrin drug tablets measured using a blue LED excited Ti-Sapphire light source and an ultra-miniature diffraction grating spectrometer.
Figure 19:
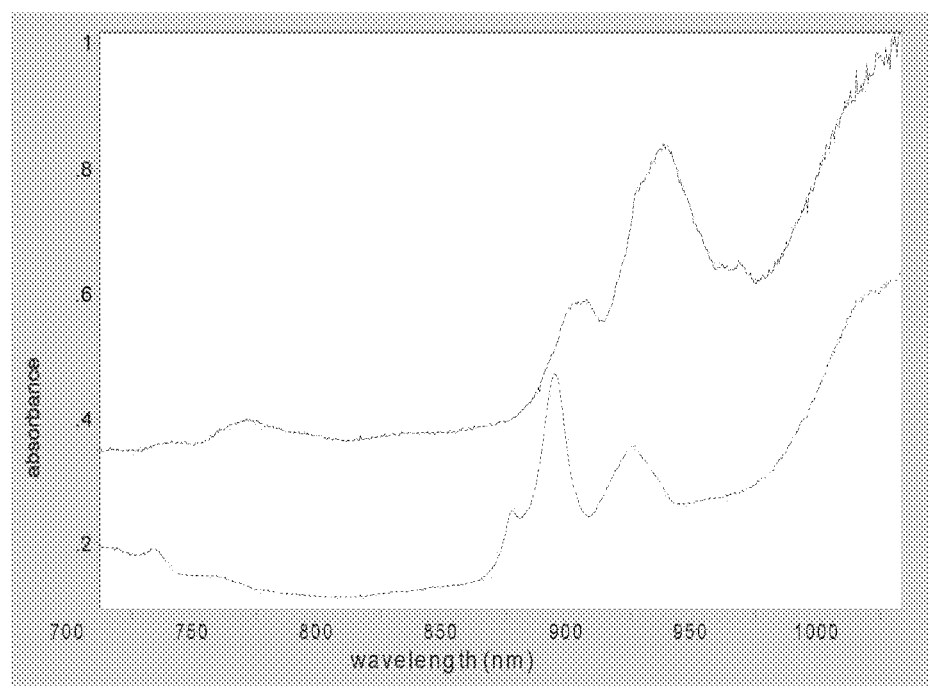
FIG. 19 shows a graph of near-infrared transmission spectrum of Tylenol and Motrin tablets measured using a commercial tungsten-halogen fiber-optic light source using 15 W of power and the same spectrometer used for the spectra in FIG. 18.

FIGS. 18 and 19 show near-infrared transmission spectra (in absorbance units) of two different drug tablets measured with both the Ti-Sapphire (FIG. 18) and the 15 W tungsten halogen (FIG. 19) near-infrared light sources. The tablets were coated Motrin (top spectrum) and uncoated 325 mg Tylenol (bottom spectrum). The major chemical component in Motrin is ibuprofen, while the major chemical component in Tylenol is acetaminophen. The drug tablet spectra were measured with the light from the near-infrared light sources transmitted all the way through the tablets. Both Tylenol and Motrin have distinct spectral signatures in the 700-1000 nm range that are related to the vibrational spectral transitions in these materials which depend primarily on the molecular structure of the active ingredients of these tablets. The Ti-Sapphire light source collection time was 9 seconds, and power consumption was 2.5 W. The tungsten-halogen light source collection time was 10 seconds, and power consumption was 15 W. The spectra in FIGS. 18 and 19 show that the spectral patterns for both drug tablets appear to be identical when measured using the two different near-infrared light sources. The signal/noise in the spectra is also very similar between the spectra measured with the two light sources.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A light source for use in spectroscopy comprising:
a single blue or blue-green high-power LED with center wavelength between 460 and 490 nm; and
a $Ti^{+3}$-Sapphire luminescent element selected from the group consisting of: a single crystal rod, a single crystal disk, a polycrystalline rod, a polycrystalline disk, a layer of $Ti^{+3}$-Sapphire powder embedded in a clear optical encapsulant, and a layer of $Ti^{+3}$-Sapphire powder mixed with one or more luminescent powders and embedded in a clear optical encapsulant;
wherein the LED light passes through the luminescent element to produce luminescent emission with continuous coverage of at least the 700-1000 nm wavelength range which is used to illuminate a sample for spectroscopic measurement.

2. The light source of claim 1, further comprising a reflector surrounding the LED and luminescent element, the reflector selected from the group consisting of a cylindrical aluminum coated reflector, a cylindrical gold coated reflector, and a cylindrical solid aluminum reflector.

3. The light source of claim 1, further comprising a transmission element positioned to relay light from the luminescent element to the sample, the transmission element selected from a single optical fiber or an optical fiber bundle.

4. The light source of claim 2, further comprising a transmission element positioned to relay light from the luminescent element to the sample, the transmission element selected from a single optical fiber or an optical fiber bundle.

5. The light source of claim 1, wherein the luminescent element is the Ti+3-Sapphire powder mixed with one or more additional luminescent powders and embedded in a clear optical encapsulant, and the one or more additional luminescent powders are rare-earth oxides or fluorescent quantum dots and that emit luminescence in the 930-1050 nm spectral range.

6. The light source of claim 2, wherein the luminescent element is the Ti+3-Sapphire powder mixed with one or more additional luminescent powders and embedded in a clear optical encapsulant, and the additional luminescent powders are rare-earth oxides or fluorescent quantum dots and that emit luminescence in the 930-1050 nm spectral range.

7. The light source of claim 1, further comprising:
a near-infrared LED with center emission wavelength in the 900-1050 nm range; and
a dichroic beamsplitter positioned to combine light from the near-infrared LED with light from the luminescent element before reaching the sample.

8. The light source of claim 1, further comprising:
a white LED with emission wavelength in the 400-700 nm range; and
a dichroic beamsplitter;
wherein the dichroic beamsplitter is positioned to combine light from the white LED with light from the luminescent element before reaching the sample.

9. The light source of claim 1, further comprising an electronic circuit included to drive the blue or blue-green LED with square or sine-wave modulated current, and wherein the light source output is square or sine-wave modulated near-infrared light.

10. A analyzer system for spectroscopy comprising:
the light source of claim 1;
a sample positioned to receive light from the light source;
a spectrometer positioned to receive light transmitted through or reflected from the sample; and
a microprocessor or computer connected to the spectrometer controlling spectral data collection and storage, wherein the microprocessor or computer stores or accesses multivariate calibration algorithms to identify materials or quantify the concentration of compounds present in the sample from spectral data acquired from the spectrometer.

11. A method of spectroscopy, comprising:

powering, with a continuous DC current, a single blue or blue-green LED having a center wavelength between 460 to 490 nm;

exciting a $Ti^{+3}$-Sapphire luminescent element with the light output of the blue or blue-green LED to produce luminescent emission continuously covering at least the 700-1000 nm wavelength range, the luminescent element selected from the group consisting of: a single crystal rod, a single crystal disk, a polycrystalline rod, a polycrystalline disk, a layer of $Ti^{+3}$-Sapphire powder embedded in a clear optical encapsulant, and a layer of $Ti^{+3}$-Sapphire powder mixed with one or more luminescent powders and embedded in a clear optical encapsulant; and directing light output of the luminescent element transmitted through or reflected from a sample to a spectrometer coupled to a microprocessor or computer for collection, storage, and analysis of spectral data for identification or quantification of one or more materials or compounds present in the sample.

12. The method of claim 11, wherein powering the blue or blue-green LED is conducted with square or sine-wave modulated current, with a modulation frequency within the 10 Hz to 10 KHz range, and further comprising synchronizing the spectrometer collection with the square or sine-wave modulation of the LED for implementation of lock-in amplification signal processing for removal of interference in the measured spectra from sunlight or room light entering the spectrometer optical input.

* * * * *